United States Patent [19]

Hoffmann

[11] 4,134,754

[45] Jan. 16, 1979

[54] METHOD OF COMBATING WILD OATS

[75] Inventor: Otto L. Hoffmann, Shawnee, Kans.

[73] Assignee: Gulf Oil Corporation, Pittsburgh, Pa.

[21] Appl. No.: 889,575

[22] Filed: Mar. 23, 1978

[51] Int. Cl.$^2$ .......................... A01N 9/20; A01N 9/02
[52] U.S. Cl. ........................................ 71/111; 71/113; 71/DIG. 1
[58] Field of Search ..................... 71/111, 113, DIG. 1

[56] References Cited
U.S. PATENT DOCUMENTS

| 2,906,614 | 9/1959 | Hopkins et al. | 71/111 |
| 3,997,322 | 12/1976 | Ratledge | 71/113 X |

Primary Examiner—Catherine L. Mills
Attorney, Agent, or Firm—Carl A. Cline

[57] ABSTRACT

The activity of barban is enhanced and variation of selectivity with climatic conditions is alleviated by applying to wild oats an effective amount of a composition comprising one part by weight barban and at least four parts by weight of a polyunsaturated fatty acid exemplified by linolenic acid. The composition is preferably either dispersed in water with the aid of an emulsifier or dissolved in a mixture of water and a volatile organic solvent such as acetone.

4 Claims, No Drawings

METHOD OF COMBATING WILD OATS

DESCRIPTION OF THE INVENTION

In the commercial use of a foliar-applied herbicide to combat unwanted vegetation many considerations are involved besides the proven efficacy of the active ingredient. Ordinarily the substance is so toxic to plants that only a small amount must be distributed uniformly over a large area, sometimes only a few ounces per acre. It is therefore necessary to use some sort of surface active agent so as to obtain uniform dispersion in a diluent, usually water, and make uniform application possible. It is not practical to make and sell the finished dispersion, ready for application, as the cost of containers and transportation would be prohibitive. The product must be packaged in relatively small containers in a physical form that is easily removed and mixed with water and will readily form an aqueous dispersion. The dispersible product is usually made and sold in the form of a solution, a stable slurry or wettable powder. There is a general tendency for active ingredients of low solubility to precipitate from solutions and slurries, forming a deposit which adheres to the wall of the container and makes it impossible to obtain a uniform aqueous dispersion. To prevent this from occurring, dispersing agents, protective colloids, solvents and various co-solvents, solutizers and other surface active agents may be added to the formulation. In almost all instances, the commercial formulation contains many ingredients and the active ingredient may not even be present in a major proportion by weight. Very often the ingredient which is present in the greatest proportion is a solvent or an inert solid, usually of a particle size in the colloidal range.

Unfortunately the other ingredients in the formulation do not usually assist the phytotoxic agent in gaining entrance through the cuticle or stomata of the plant so as to kill the plant by interfering with some essential biological process. At best, the surface active agents, solvents and diluents behave generally as excess baggage. At worst, they may actually interfere with the entrance of the herbicide into the plant and promote washing off by the first shower. It is often observed that the efficacy and selectivity of a herbicide formulation changes radically if there is a small change in the weather. Abnormally low or high temperatures during a period of several days prior to application may greatly reduce or increase efficacy. Examination of sprayed plants may indicate that application of the herbicide was done efficiently and that the customary amount of herbicide is initially present on the surface of the plants, but the herbicide does not have the usual effect. Apparently the plants undergo changes under the stress of cold weather and other conditions which render them more or less resistant to the herbicide.

Barban (4-chloro-2-butynyl m-chlorocarbanilate) is customarily applied in an aqueous dispersion to wheat fields containing wild oats, when the wild oats are in early stages of growth. It has been observed that if the wheat has been subjected to low temperatures during most of its previous growth, it is unusually susceptible to injury by the barban, whereas efficacy on wild oats shows little change. I have discovered that under these conditions efficacy of barban on wild oats can be increased and application rate can be reduced so as to alleviate injury to wheat if the barban is applied in combination with a substantial amount of an unsaturated long chain fatty acid containing at least two and preferably three olefinic bonds.

Briefly, the improved method of this invention consists of applying to wild oats plants an effective amount of a composition comprising one part by weight barban and at least four parts per weight of a polyunsaturated fatty acid selected from the group consisting of linoleic and linolenic acids. Although linolenic acid is preferred, it is more convenient and economical to employ a mixture of the two acids in the form which is marketed as linseed oil fatty acids.

Unsaturated fatty acids have been employed as co-solvents in herbicide formulations in the past, as, for example in U.S. Pat. Nos. 3,709,676 and 3,628,942. Almost every organic liquid which is non-toxic to humans and has some solvent ability has in fact been tried from time to time in attempts to improve some herbicide formulations. The reactive unsaturation of linoleic and linolenic acids has also been employed in some formulations to remove odor-causinng substances, as in U.S. Pat. No. 3,961,043. However, the improvement in the action of barban on wild oats by use of these acids has not been previously suggested.

It is preferred to make up a spray mixture of the barban-linolenic acid composition in as simple a manner as possible, since additional ingredients in general interfere with the desired phytotoxic effect. The barban-linolenic acid composition may be put into solution in water with the aid of a volatile alcohol, ketone or ester solvent, such as acetone, methanol or methyl acetate, or may be dispersed in water with the aid of an emulsifier. It is preferred to use small spray volumes, as for example ten gallons per acre or less so as to obtain the desired effect with as little pollution of the environment as possible. The method of this invention is particularly suitable for use with low volume rotary disc spray apparatus. By use of this technique it is feasible to apply finished spray mixtures at spray volumes as low as one quart per acre. (2.34 liters per hectare).

The upper limit of polyunsaturated fatty acid employed in combination with barban should be adjusted so that no more than four pounds of polyunsaturated fatty acid is applied to an acre of a crop containing wild oats, so as to limit injury to the crop.

Below are described the results of comparative tests of the method of this invention in comparison with use of a commercial formulation of barban of a type disclosed in U.S. Pat. No. 2,906,614. The tests were conducted during weather of the type which was considered likely to produce variations in barban selectivity, with an increased probability of injury to wheat.

Use of Barban-Linolenic Acid Composition on Wild Oats

Two rows each of Cherokee oats and Rolette durum wheat were seeded on three dates, April 1st, 5th and 9th. After the plants had emerged and grown to a size suitable for application of barban, eleven separate treatments with six different formulations were applied on April 26th. In general, the weather was damp, cold and variable, as follows:

Weather Information

April 26 (application day) — wet from week-end rains; dew on plants until 0945; cloudy with temperature in 50°'s(° F.)
April 27–8 — Cool (40°'s) (° F.) cloudy, rainy
April 29 — Cool and sunny May 2-3 — Frost (26° F.)

The barban formulation used as a standard was a commercial emulsifiable concentrate, diluted with water to the desired concentration.

The five experimental formulations were made by dissolving barban in a mixture of 87.4 percent linolenic acid and 12.6% acetone in concentrations ranging from one ounce to one pound of barban per gallon. These formulations were then diluted with a 30 percent solution of acetone in water to obtain the desired application rate at a spray volume of 5 gallons per acre.

The results of the tests were evaluated on May 21st. These results are summarized in the following table, using a scale of zero=no injury to 10=complete control.

| Treatment Formulation | Barban Rate (lb/A) | Plant Injury at Various Planting Dates | | | | | |
|---|---|---|---|---|---|---|---|
| | | April 1 | | April 5 | | April 9 | |
| | | Wheat | Oats | Wheat | Oats | Wheat | Oats |
| Standard | 1/4 | 4 | 10 | 5 | 10 | 4 | 9 |
| Exp. (1 lb/gal) | | 8 | 10 | 5 | 10 | 6 | 10 |
| Standard | 1/8 | 1* | 9* | 1* | 9* | 2* | 9* |
| Exp. (1/2 lb/gal) | | 6 | 9 | 4 | 9 | 5 | 9 |
| Standard | 1/16 | 2* | 7* | 0 | 5 | 1* | 8* |
| Exp. (1/4 lb/gal) | | 5 | 9 | 1* | 8* | 4 | 9 |
| Standard | 1/32 | 2 | 4 | 0 | 4 | 0 | 5 |
| Exp.(1/8 lb/gal) | | 3* | 8* | 1* | 8* | 2* | 8* |
| Standard | 1/64 | 0 | 2 | 1 | 4 | 0 | 3 |
| Exp.(1/16 lb/gal) | | 2* | 8* | 1* | 7* | 0* | 8* |
| Check (no treatment) | — | 0 | 0 | 0 | 0 | 0 | 0 |

*Acceptable treatments (i.e., wheat injury of 3 or less and oat control of 7 or more.

It can be seen from these results that acceptable results were obtained with a barban-linolenic acid combination at an application rate of only 1/64 lb. barban per acre. In case of error in application, wild oats that receive only half this much of the improved composition will also exhibit acceptable control and an accidental overlap which receives twice this application rate will not produce excessive injury on wheat. In other words, the 1/64th lb. per acre rate can be used with a comfortable margin for error. It will also be seen that the standard formulation does not tolerate errors of this magnitude while still giving acceptable control of oats at all three stages of growth in the test.

I claim:

1. In the method of selectively killing wild oats by post-emergent application of barban to wild oats in the second leaf stage, the improvement consisting of applying to wild oat plants an effective amount of a composition comprising one part by weight of barban and at least four parts by weight of a polyunsaturated long chain fatty acid selected from the group consisting of linoleic and linolenic acids.

2. The improvement of claim 1 consisting of applying to the wild oats in the presence of wheat a composition comprising one part by weight of barban and at least four parts by weight linolenic acid in combination with water and a volatile ketone or ester solvent.

3. The improvement of claim 1 consisting of applying to the wild oats in the presence of wheat a composition comprising one part by weight of barban and at least four parts by weight of linolenic acid in combination with water and acetone.

4. The improvement of claim 1 consisting of applying to the wild oats in the presence of wheat a composition comprising one part by weight of barban with at least four parts by weight of linolenic acid in combination with water and acetone at an application rate of from one sixty-fourth on one-sixteenth pound of barban per acre.

* * * * *